United States Patent
Mansmann et al.

(10) Patent No.: US 8,858,632 B2
(45) Date of Patent: Oct. 14, 2014

(54) IMPLANTS FOR REPLACING HYALINE CARTILAGE, WITH HYDROGEL REINFORCED BY THREE-DIMENSIONAL FIBER ARRAYS

(75) Inventors: Kevin Mansmann, Paoli, PA (US); Peter Popper, Wilmington, DE (US)

(73) Assignee: Formae, Inc., Paoli, PA (US)

( * ) Notice: Subject to any disclaimer, the term of this patent is extended or adjusted under 35 U.S.C. 154(b) by 1180 days.

(21) Appl. No.: 11/390,539

(22) Filed: Mar. 23, 2006

(65) Prior Publication Data
US 2007/0224238 A1    Sep. 27, 2007

(51) Int. Cl.
| | | |
|---|---|---|
| A61F 2/30 | (2006.01) | |
| A61F 2/38 | (2006.01) | |
| A61L 27/16 | (2006.01) | |
| A61L 27/18 | (2006.01) | |
| A61L 27/44 | (2006.01) | |
| A61L 27/52 | (2006.01) | |
| A61F 2/46 | (2006.01) | |

(52) U.S. Cl.
CPC ......... *A61F 2/30756* (2013.01); *A61F 2/30965* (2013.01); *A61L 27/16* (2013.01); *A61L 27/18* (2013.01); *A61L 27/446* (2013.01); *A61L 27/52* (2013.01); *A61F 2/30767* (2013.01); *A61F 2/3094* (2013.01); *A61F 2/468* (2013.01); *A61F 2002/30093* (2013.01); *A61F 2002/302* (2013.01); *A61F 2002/30457* (2013.01); *A61F 2002/30892* (2013.01); *A61F 2002/30914* (2013.01); *A61F 2002/30957* (2013.01); *A61F 2002/4635* (2013.01); *A61F 2210/0019* (2013.01); *A61F 2220/0058* (2013.01); *A61F 2230/0065* (2013.01); *A61L 2430/06* (2013.01)
USPC ................... 623/11.11; 623/14.12; 623/23.72

(58) Field of Classification Search
CPC ............................................. A61F 2002/30761
USPC ................................ 623/14.12, 23.72, 11.11
See application file for complete search history.

(56) References Cited

U.S. PATENT DOCUMENTS

| | | | |
|---|---|---|---|
| 6,946,003 B1 * | 9/2005 | Wolowacz et al. | 623/23.72 |
| 2002/0022884 A1 * | 2/2002 | Mansmann | 623/14.12 |
| 2002/0173855 A1 * | 11/2002 | Mansmann | 623/23.72 |

* cited by examiner

Primary Examiner — Randy Shay
Assistant Examiner — Dinah Baria
(74) Attorney, Agent, or Firm — Duane Morris LLP

(57) ABSTRACT

Implants with hydrogel layers reinforced by three-dimensional fiber arrays can replace hyaline cartilage. Such implants should replace an entire cartilage segment, rather than creating a crevice around a plug, so these implants must be thin and flat, they must cover large areas, the tips of any tufts or stitches must not reach the hydrogel surface, and they must be flexible, for arthroscopic insertion. The use of computerized stitching machines to create such arrays enables a redesigned and modified test sample to be made with no delays, and no overhead or startup costs. This provides researchers with improved tools for making and testing implants that will need to go through extensive in vitro, animal, and human testing before they can be approved for sale and use. Fiber-reinforced hydrogels also can be secured to strong shape-memory rims, for securing anchoring to bones.

14 Claims, 3 Drawing Sheets

IMPLANTS FOR REPLACING HYALINE CARTILAGE, WITH HYDROGEL REINFORCED BY THREE-DIMENSIONAL FIBER ARRAYS

FIELD OF THE INVENTION

This invention is in the field of surgical implants, and relates to implants that contain synthetic hydrogel layers for replacing cartilage in joints such as knees, hips, or shoulders.

BACKGROUND INFORMATION

There are four major types of cartilage in mammals. Hyaline cartilage is the only type of cartilage covered by this current invention, and a brief description of why it is different from the other three types of cartilage is necessary, to help the reader understand the invention and compare it against the prior art.

Hyaline cartilage is the main type of cartilage that provides smooth, slippery, lubricated surfaces that slide and rub against other cartilage surfaces in "articulating" joints, such as knees, hips, shoulders, etc. It is formed as a relatively thin layer (usually no more than about 3 or 4 millimeters thick) that covers certain surfaces of hard bones. While the hyaline cartilage in some joints (such as fingers) is not heavily stressed, the hyaline cartilage in other joints (notably including knees and hips) is frequently and repeatedly subjected to relatively heavy compressive loads, shear forces, and other stresses, and it does not have a blood supply or cellular structure that enables the type of cell turnover and replacement that occurs in most other tissues. As a result of those and other factors, hyaline cartilage in knees and hips needs repair or replacement at fairly high rates among the elderly (due to gradual wear, injury, disorders such as osteoarthritis or rheumatoid arthritis, etc.), and at lower but significant rates among younger patients (due to injury, congenital joint displacements that lead to unusual wear patterns, etc.).

Since this invention relates to fiber reinforcing layers for hydrogel components of implants, it is important to recognize that hyaline cartilage is present only in relatively thin layers that coat the surfaces of bones. Since it is a soft tissue that cannot repair itself, it is vulnerable to damage when subjected to repeated loadings and stresses, and it would be even more vulnerable to damage if it were present in thick layers. As a result, the fiber reinforcing layers disclosed herein are subjected to crucially important constraints, when it comes to thickness.

Meniscal cartilage refers to specialized arc-shaped segments that help stabilize the knee and shoulder joints. Like hyaline cartilage (and unlike elastic cartilage or spinal cartilage), they have smooth lubricated surfaces that slide and rub against other cartilage surfaces, when a joint is moving. They are made of a highly fibrous form of cartilage, which is affixed to hard bone mainly via long fibers that extend out of the tips of the arcs, while the peripheral surfaces of the arcs are affixed to soft tissues instead of bone. In the shoulder joints, these arc segments are called labrum (or labral) segments; however, since their shapes and structures are nearly identical to meniscal segments in knees, and since labral cartilage in shoulders need to be repaired only rarely compared to meniscal cartilage in knees, labral cartilage usually is included in the term "meniscal cartilage".

Because of their arc shapes, meniscal cartilage segments have roughly triangular cross-sections, and their center regions have greater thickness than the hyaline cartilage layers that cover the surfaces of bones in joint regions. While the methods disclosed herein can be adapted to enable the creation of all or at least a portion of a three-dimensional fiber array that will have the proper shape and thickness for reinforcing a meniscal segment (indeed, early prototypes have been created with such shapes, which appear to be satisfactory for such use), the focus of this invention at the current time and as disclosed herein is on creating three-dimensional fibers arrays that have suitable thicknesses for reinforcing the relatively thin layers that characterize hyaline cartilage.

This invention specifically excludes two other types of mammalian cartilage, which have very different sizes, shapes, and structural requirements than hyaline cartilage (or meniscal cartilage). A brief discussion of those two excluded types of cartilage can help the reader better understand the invention, the obstacles it must overcome, and why a number of items of prior art, developed for those other two types of cartilage, become irrelevant and even misleading when considered in the context of attempts to repair hyaline cartilage.

In particular, the spinal discs (which separate the vertebral bones) are made of a completely different type of cartilage, and they have no smooth and slippery surfaces. Instead, the spinal discs must completely prevent any sliding or "shearing" motions between adjacent vertebral bones, since any such sliding motions could pinch and severely damage or even sever the spinal cord. Therefore, the cartilage in the spinal discs is heavily reinforced by long fibers that emerge from the vertebral bones and penetrate essentially all the way through each spinal disc. In addition, the spinal discs are substantially thicker than hyaline cartilage segments. Both of those factors enable the manufacture of strong reinforced implants for repairing spinal discs, in ways that are simpler and easier than providing adequate reinforcing layers that must be kept thin and that cannot have any roughness on a smooth and lubricated surface. In repairing a spinal disc, the real challenge is in protecting the spinal cord, rather than in providing adequate materials for replacing the disc. This is reflected in the fact that spinal discs are repaired by neurosurgeons, while joint cartilage is repaired by orthopedic surgeons.

Elastic cartilage (i.e., the type of cartilage that gives shape to certain body parts such as the ears and nose) also is very different from hyaline cartilage, in both structure and function. Unlike cartilage in joints, elastic cartilage is not subject to wear and degradation; nevertheless, it sometimes needs to be repaired, usually to reshape ears or noses that were injured in accident victims, burn patients, etc. Elastic cartilage does not need to withstand any significant compressive or shearing loads or stresses, so implants for repairing elastic cartilage only need to meet low and minimal requirements for strength, toughness, and durability. In addition, elastic cartilage does not have smooth sliding surfaces that must be carefully protected.

Accordingly, only a set of very low and relaxed structural and physical requirements apply to elastic cartilage, compared to hyaline or meniscal cartilage in load-bearing joints such as knees. That set of very low mechanical and strength requirements has led to extensive research in regenerating elastic cartilage in ears and noses, using transplanted cells that are temporarily protected by synthetic implants that are designed to be digested, resorbed, and replaced by natural tissue during a span of several months following surgical implantation.

However, two factors can help illustrate and explain the problems that make hyaline cartilage repair, in dynamic joints, much more difficult than elastic cartilage repair, in inert and non-stressed locations such as an ear or nose.

The first factor is this: in hyaline cartilage in "loaded" joints such as knees, chondrocyte cells will not actively secrete the "building block" molecules that are assembled into cartilage, unless they are "activated" by stresses imposed on the bones. Compressive stresses in particular trigger certain signaling mechanisms, which cause chondrocyte cells to respond by secreting the building blocks of cartilage.

However, implants that carry transplanted cells must be very careful about imposing compressive loads on the implants. Such implants need to be at least somewhat soft and non-rigid; otherwise, they would scrape, abrade, and damage any opposing cartilage surfaces they rub against. However, if compressive loads are imposed on a soft and non-rigid implant carrying transplanted cells, the compressive loads will pose major risks of damaging the implant, by squashing and killing the cells in the implant, or by squeezing the cells out of the implant.

This leads to a difficult balancing act. Despite the best efforts of many hundreds of researchers and surgeons, implant devices carrying transplanted cells can be used to regenerate hyaline cartilage, only when relatively small defects (usually caused by physical injuries) are involved. Furthermore, because recovery and rehabilitation is slow and gradual, and requires months after surgery is performed, cell transplant approaches usually are considered as an option only if a patient is relatively young (such as under the age of about 55 or 60), and is not carrying substantial excess weight. This eliminates most people older than about 60, and people who are overweight, as candidates for cartilage repair using cell transplantation. That creates major limitations, since patients older than about 60, and patients who are overweight, comprise the very large majority of people who suffer from serious cartilage problems in their knees and hips.

A second obstacle that arises, in repairing hyaline cartilage in moving joints, involves the eventual fates of "resorbable" implants, which are made of specialized materials (such as poly-glycolic acid combined with collagen fibers) that are slowly digested and dissolved by enzymes in body fluids, over a span of months. This type of digestion and replacement enables resorbable implants to be gradually replaced by natural tissue, which is almost always preferable to a synthetic foreign implant, where feasible. However, biological resorption and replacement can lead to the release of fragments and debris, after a synthetic material passes a midway point of being partially broken apart and digested by enzymes. In an inert location such as a segment of elastic cartilage in a nose or ear, such fragments and debris will not cause serious problems. However, if fragments and debris from a partially-resorbed implant were released into a moving joint such as a knee, they might begin abrading and damaging the smooth cartilage surfaces that are pressing, sliding, and rubbing against each other.

It may be possible to overcome these problems, if certain types of reinforcing fiber materials in combination with resorbable hydrogels are used. For example, one approach that holds potential is to make a reinforcing fiber array from non-resorbable fibers that are biocompatible and that can encourage cell growth within the fiber array, while making the hydrogel from a material that can be dissolved and replaced. An enormous amount of research is actively being done on "tissue engineering", using in vitro cell culturing methods, devices, and reagents to grow cells outside the body, but within matrix-type materials that will enable cell-carrying implant devices to be implanted into a body. Therefore, the current invention focuses upon and is limited to nonresorbable 3D fiber arrays, which have been or can be coupled to bone-anchoring devices that are designed to last for decades (preferably for the entire remaining life of any patient); however, the hydrogel material itself, which will need to be reinforced by a 3D fiber array as described herein, is not limited to nonresorbable synthetic hydrogels only, and might be provided by collagen, polyglycolic acid, or other types of resorbable fibers or polymers.

In view of the major differences between hyaline cartilage versus spinal or elastic cartilage, it must be understood that: (i) efforts that have been made to repair elastic or spinal cartilage cannot be simply or readily adapted to repairing hyaline cartilage, which must overcome very different problems and operating constraints in joints such as knees or hips; (ii) all discussion and claims below, and all subsequent references to cartilage herein, are limited solely to hyaline cartilage; and, (iii) all references herein to implants are limited to nonresorbable synthetic implants for replacing hyaline cartilage.

In addition, all teachings and claims herein are expressly limited to surgical implants that contain hydrogel components. To qualify as a hydrogel, a material must have the types of physicochemical properties that are regarded as "gelatinous" by people skilled in materials science. That term refers to a type of semisolid resilience that is different and distinct from (for example) a piece of fabric or sponge that has been saturated with water. Although fabrics, sponges, and various other materials can enable the passage of water molecules through those materials, they do not have the type of structural properties or physical and mechanical traits and behavior of gelatinous materials.

Most hydrogels that have substantial tensile strength (which are the only hydrogels of interest herein) hold water molecules within a cohesive polymeric molecular matrix, in a way that enables the travel of the water molecules through the molecular matrix. Although such hydrogel materials must have at least some degree of deformability, they cannot be in liquid form, and they must return to a specific nondeformed shape after any loads or stresses have been removed. A different class of colloidal suspensions (often called "thixotropic" materials) can also form hydrogels when allowed to sit in stationary form, but they do not have substantial tensile strength, and they will convert into liquids if subjected to shearing stresses, so they are not of interest herein.

In natural cartilage, the hydrogel structure is created by a three-dimensional matrix that is given shape and strength mainly by collagen, the fibrous protein that holds together nearly all soft tissues in animals. In synthetic hydrogels, the three-dimensional matrix usually has a molecular structure made of complex polymers that have a combination of: (i) long continuous chains (often called "backbone" chains), containing mainly carbon atoms and sometimes containing oxygen, nitrogen, sulfur, or other atoms as well; (ii) side chains, which branch off the "backbone" chains in ways that can have either controlled or semi-random spacing, length, content, etc.; and, (iii) crosslinking bonds, which connect the backbone and side chains to each other in ways that create complex three-dimensional molecules that have sufficient spacing between them to allow water molecules to travel within the molecular matrix.

Synthetic hydrogel polymers must be hydrophilic, to cause them to attract and hold water molecules. This can be accomplished by including large numbers of oxygen atoms (usually in hydroxy groups), nitrogen atoms, or other non-carbon atoms in the backbone and/or side chains, to provide "polar" groups that will attract water, a polar liquid. This aspect of polymer chemistry is well known, and hydrophilic formulations of various candidate polymers are well-known and available.

Fluid permeability (which involves the ability of water to pass through the molecular matrix of cartilage) is important in the behavior and performance of natural cartilage. As an example, FIG. 6 in U.S. Pat. No. 6,530,956 illustrates how fluid flow through cartilage can help distribute and "smooth out" the peak pressures that are imposed on cartilage in a load-bearing joint such as a knee, when a person begins walking or running.

Even more importantly for the purposes of this invention, synthetic hydrogel polymers are flexible, and can be rolled into cylindrical forms that can be inserted into a joint that is being surgically repaired, via a minimally-invasive incision, using an arthroscopic insertion tube. By avoiding and eliminating the need for "open joint" surgery, arthroscopic insertion of a flexible implant in a rolled-up cylindrical form can spare surrounding tissues and blood vessels from severe damage during the surgical operation.

Due to these and other factors, hydrogel materials are of interest in joint repair implants, and may be able to provide better performance than the solid plastics (such as high molecular weight polyethylene, abbreviated as HMWPE) that are used today in most hip and knee replacements.

However, because water molecules make up a substantial part of their volume and weight, hydrogels are substantially weaker than solid plastics that do not contain any water. Accordingly, hydrogels have not been strong enough or durable enough, in the past, to offer realistic and practical alternatives to hard plastics, for use in implants for repairing or replacing hyaline cartilage in joints such as knees or hips.

The foregoing statement needs to be qualified, by mentioning a specific type of surgical implant that is available in Europe and Canada, but not in the United States. These implants are sold by a company called SaluMedica (Atlanta, Ga.), under the trademark SALUCARTILAGE. They are described in the SaluMedica website (www.salumedica.com) as being made from the same class of polymers in flexible contact lenses, but with denser formulations having greater strength. It appears that these implants are made in cylindrical shapes only, with enough length (or thickness) to cause them to remain in place without requiring any additional anchoring attachments, if inserted into a properly prepared cylindrical hole that is created by a surgeon in the surrounding cartilage.

However, none of the supporting articles cited in the SaluMedica website could be located in a search of the database of the National Library of Medicine. Instead, other articles (such as Lange et al 2005 and Meyer et al 2005) were located which reported that serious problems have arisen when such implants are used, including dislodgement and/or apparently total destruction of such implants in some patients who receive them, apparently due to "the inadequate connection to the bone with risk of dislocation". Apparently because of these limitations, statements on the SaluMedica website indicate that the company is not even attempting to obtain approval for use of those devices in the United States.

It must also be noted that the SALUCARTILAGE implants are available, only in the form of partial "plugs", which must be inserted into a hole that is created by a surgeon, in the surrounding cartilage area. Whenever that type of "plug" approach is used, it creates a circular seam or juncture between (i) the outer top surface of the inserted synthetic plug, and (ii) the surrounding natural cartilage. This seam or juncture cannot and will not have the level of smoothness of a normal undamaged hyaline cartilage surface; instead, even under the best of conditions, it will have the shape of a small gap or trench, surrounding the artificial plug. Over a span of years or decades, any discontinuity in the surface of a "repaired" cartilage segment will pose a serious risk of abrading and damaging the natural cartilage surface that presses, rubs, and slides against the modified surface.

The only way to avoid that type of problem is by replacing an entire cartilage segment, rather than by inserting a plug into the middle of a cartilage segment (in the case of femoral runners, this can be done by a "unicompartmental" repair, but that still requires replacement of either an entire medial segment, or an entire lateral segment). The implants described herein, which are manufactured in relatively thin and wide sheets rather than small plugs, are ideally suited to enable the replacement of entire cartilage segments, rather than merely inserting plugs into holes that have been cut into surrounding cartilage segments.

Indeed, in most cases, the preferred procedure is to replace both of the two cartilage segments that rub against each other in a joint, in a single surgical operation. This preference arises from the fact that as soon as one cartilage surface becomes damaged, it loses its smoothness, and begins to abrade and damage the other cartilage surface that it rubs against. Accordingly, because any surgical operation inflicts damage on the tissues and blood vessels surrounding a joint (and causes pain and discomfort, and requires a rehabilitation period), it usually is better to replace both surfaces in a single operation, rather than repairing one damaged surface in first operation, and then have to repair a second damaged surface in second operation a short time later. Accordingly, the plug-type hydrogel implants being sold by SaluMedica (for sale only outside the US) are very different from the thin sheets being developed by the inventors herein.

The recent and ongoing efforts to provide improved hydrogel implants for replacing cartilage in joints by Mansmann (the first-named inventor herein) are described in U.S. Pat. No. 6,629,997 ("Meniscus-type implant with hydrogel surface reinforced by three-dimensional mesh") and published applications 2002-0173855 ("Cartilage repair implant with soft bearing surface and flexible anchoring device"), 2002-0183845 ("Multi-perforated non-planar device for anchoring cartilage implants and high-gradient interfaces"), and 2004-0133275 ("Implants for replacing cartilage, with negatively-charged hydrogel surfaces and flexible matrix reinforcement"), all of which are available from the US Patent and Trademark Office website, www.uspto.gov. The contents of those published items are incorporated herein by reference, as though fully set forth herein.

Much of that work has focused on hydrogels made from a class of polymers known as polyacrylonitriles (abbreviated as PAN). This class of acrylic derivatives formed the main component of certain types of synthetic fibers that formerly were sold by the DuPont company, under the trademark ORLON™. Other known hydrophilic polymers, including various forms of polyurethane, also offer candidate materials for use in forming hydrogels with enough strength for use as described herein. These polymers can be formulated in ways that will create molecular matrices having gelatinous properties, when hydrated.

Because hydrogel polymers (which must, by definition, contain substantial quantities of water molecules) will inevitably be weaker than various known types of hard plastics that do not contain any free water, the work by Mansmann has focused on hydrogels that are reinforced by three-dimensional fiber arrays, made of synthetic fibers having high tensile strength.

One method of fabricating such 3D fiber arrays, which was identified in the above-cited patent applications, is a three-dimensional weaving method used by a company called TechniWeave (a division of Albany International), to create high-strength composite materials for applications such as aeronautics and astronautics. However, as that process was evaluated in more detail, it became clear that it is not well-suited for medical devices that will need to go through a long and extensive process of in vitro testing, animal testing, and human clinical trials, before any such implant can be approved for use in human patients.

A major problem arises from the fact the prototypes that will be made and tested, in in vitro and then animal tests, are likely to be modified somewhat, each time more data and performance results become available from a previous series of tests. If a 3D weaving process is used, each newly-modified prototype will incur relatively high setup and startup costs. This is comparable to the costs of manufacturing operations that use molding technology, in which a new set of molds must be created each time a customer wants to modify an item being produced, even if the modification is only minor.

Accordingly, even though the TechniWeave process (or other similar processes) may be well-suited for manufacturing large numbers of units after a final design has optimized, it is not well-suited for developing and testing a series of prototypes that will undergo multiple changes, as prototypes are designed, made, and tested, and then redesigned, modified, and tested again based on earlier results. Therefore, other methods for making candidate reinforcing materials, with lower overhead-type startup costs, had to be identified and evaluated.

Faced with that challenge, the first-named inventor (an orthopedic surgeon) identified and hired a consultant (the second-named inventor herein) who is an expert in fibers and textiles, and who has extensive experience in developing ways to make articles having substantial thickness and controllable shapes, as described in patents such as U.S. Pat. No. 4,719,837, U.S. Pat. No. 5,470,629, and U.S. Pat. No. 6,579,815, Patent Cooperation Treaty application WO 89-01320, and European patent EP 375729 (all invented or coinvented by Popper).

Before the results of their joint efforts (which led to the invention herein) are described, several concepts and terms needs to be established, in two very different fields: (i) the structure and arrangement of normal and natural biological cartilage, in healthy mammalian joints, and (ii) means for assembling fibers into fabrics, textiles, carpets, and other materials. The following subsections address those two areas.

Condyles and Collagen Fibers in Natural Cartilage

Any bone surface that is covered by a layer of hyaline cartilage is referred to herein as a "condyle". However, it should be noted that this term is not always used consistently, by physicians and researchers. Some users limit "condyles" to the rounded ends of elongated bones; this clearly includes the long bones in the arms and legs, it usually but not always includes smaller elongated bones in the hands, fingers, feet, and toes, and it clearly excludes the cartilage-covered "sockets" in the ball-and-socket joints of the hips and shoulders. By contrast, other authors use "condyle" to refer to any bone surface covered by hyaline cartilage, including the socket surfaces in hip and shoulder joints. Since reinforced hydrogels as disclosed herein can be used to replace hyaline cartilage segments on any bone surface, the broader definition (which covers any bone surface covered by hyaline cartilage, including long bones, finger joints, socket surfaces in hips and shoulders, etc.) is used herein.

Any condylar surface contains a transition zone, called the subchondral layer or zone, at the interface between the hard bone and the cartilage. This transition zone strengthens and reinforces the cartilage, to ensure that the cartilage (which is relatively soft) is not simply pushed or scraped off the supporting bone when a joint is subjected to loading and shearing stresses. In the transition zone, large numbers of microscopic collagen fibers, firmly anchored in the hard bone, emerge from the bone in an orientation that is generally perpendicular to the bone surface at that location.

When rounded surfaces are involved, that direction is called radial; the surface-parallel direction at any point on a rounded surface is called tangential. For convenience, all descriptions and drawings herein assume that a bone surface is positioned horizontally, with a layer of cartilage resting above it and on top of it, and with the smooth articulating surface of the cartilage as the upper exposed surface of the structure.

When described in that orientation, as collagen fibers rise through the cartilage and approach the smooth articulating surface of the cartilage covering layer, they go through a rounded transition, and become tangential to the articulating surface of the collagen. This is shown in photographs (taken by electron microscopes) of collagen fibers in hyaline cartilage segments, which are available in sources such as Clark et al 1990 and 1991. The tangential orientation of the collagen fibers on the surface of the cartilage helps create and sustain a smooth surface on the cartilage.

Fibers, Yarns, Fabrics, and Fiber Arrays

This section briefly reviews a number of terms and concepts in the field of fibers, fabrics, textiles, and "fiber arrays".

As used herein, "fiber" includes long flexible strands of material that are suited for weaving, knitting, or other assembly into fabrics, textiles, carpets, or other fiber arrays. Most synthetic fibers are manufactured with essentially round cross-sections, although that is not necessary. They can be cut into any desired length after manufacture, and they typically are manufactured in continuous lengths, which are stored on spools, cores, or similar devices to facilitate handling and use.

The term "yarn" refers to a bundle or other relatively cohesive cluster of fibers, in which the fiber bundle comprises a generally cylindrical but flexible enlarged strand. Most synthetic fibers used to make conventional fabrics, textiles, or carpets are too thin to work with efficiently, in "monofilament" form. Therefore, they usually are twisted, braided, or otherwise manipulated in ways that create larger aggregated strands, called yarns, which are easier to handle and work with than very thin individual fibers. However, some types of polymer fibers can be made in any desired thickness (comparable to monofilament fishing lines having a range of diameters and tensile strengths). Accordingly, references herein to "fiber" or "fibers" (or similar terms, such as threads, strands, etc.) can include monofilament fibers, yarns, or any combination of the two.

The term "thread" is used herein to refer to a strand of fiber (either monofilament, or yarn) that is affixed to a backing layer by means of stitching, and or that otherwise passes through an eye of a needle during a manufacturing operation. This term, which arises from the conventional "needle and thread" pairing, distinguishes threads from other fibers that are woven or knitted into a fabric.

A very broad term, used herein to refer to and include any type of material that is manufactured from fibers in a controlled manner, is "fiber array". Array derives from the same word as "arranged", and the two words have essentially the same breadth. Arrays can include any type of fabric, mesh, carpet, or other textile or similar material made of a fibrous material that is somehow arranged (or arrayed) in a desired and controlled manner. Some fiber arrays have a relatively flat and mainly two-dimensional form, such as a single-layer woven, knitted, or similar fabric. Other fiber arrays have three-dimensional shapes where substantial thickness is crucial to their performance, such as in tufted carpets. Still other fiber arrays sit at various midpoints in the range from very thin to very thick, as occurs with knitted fabrics made from yarns with substantial thickness. Fiber arrays also can be made by means such as chemical treatments (using glues, adhesives, etc.), energy input (such as heat or radiation to cause partial melting and bonding of some fibers), or mechanical means other than stitching or tufting (such as needle-punching, using air to form a layer of "batt" material on the surface of a screen, etc.), to fix and set an array of fibers into the cohesive structure of an array.

As used herein, the term "fabric" refers to a relatively thin and flat fiber array, of a type that can be created by means such as conventional weaving, knitting, etc. "Fabric" is intended and used herein to distinguish relatively thin, essentially two-dimensional sheets of material, from thicker materials.

Thicker materials, in which thickness (which might also be referred to as height, depth, or similar terms) plays an important role and is deliberately created by means that extend beyond methods such as conventional weaving or knitting, are referred to herein as "three-dimensional arrays" (abbreviated as 3D arrays). As examples, any tufted material (such as a carpet) is a 3D array, since tufts are deliberately designed to extend a significant distance above or below a backing layer. An embroidered or other stitched material that adds additional fibers to a backing layer will become a 3D array, if any steps are taken to use either: (i) fibers with sufficient thickness to add significant height or depth, above or below the backing layer; or (ii) processing steps to create stitches, loops, tufts, or other structures that extend a significant distance above or below a backing layer of flat fabric. Similarly, materials made by stacking two or more layers of fabrics (or fibers) on top of each other would be regarded as 3D arrays, rather than flat fabrics. A piece of flat fabric does not become a 3D array merely because it is bent, curved, or folded, especially if such steps are reversible; however, 3D arrays can have controlled shapes, curvatures, contours, etc.

The term "backing layer" (or backing material) is used herein to refer to a piece of fabric or other sheet-type material that undergoes a stitching, embroidering, tufting, gluing, or similar process that affixes additional fibers to the backing layer. In some cases, a sheet of plastic, paper, or similar material can be used as a backing layer; this can be useful, if the backing layer is to be dissolved and removed in a subsequent step, to create an embroidered item having an "open" structure. However, in most cases, a woven fabric is used, to minimize the risk that the backing layer might suffer from damage, distortion, or a loss of integrity due to repeated puncturing by a sharp needle.

Stitching refers to the process of using one or more needles to repeatedly push one or more fibers through a backing layer. Various types of stitching are known, and two important classes of stitched materials are referred to herein as "tufted" and "sewn" arrays. The difference between those two types of fiber arrays is explained below, after the basic operating mechanism of stitching machines has been explained.

Computerized Stitching Machines

Various types of stitching machines (including programmable computer-controlled and/or robotic stitching machines) have been developed, for uses other than this invention. Since these types of machines can be adapted for use as described herein, they need to be briefly reviewed.

The discussion herein focuses on a specific type of machine called an AMAYA™ embroidery machine, which is made and sold by a company called Melco (www.melcousa.com), a subsidiary of a company called Saurer (www.saurer.com). The AMAYA system is designed to be modular, allowing a person or company to buy or lease a single unit; later, the person or company can buy or lease additional machines and hook them up together, so that multiple units can work together to create exceptionally complex items. The trademark AMAYA is an acronym for the phrase, "as many as you add", to emphasize the modular nature of these machines. These machines are illustrated and described on Melco's website, and they are readily available in both new and used models. Training courses and videos that can help operators learn to use them also are available (any references herein to "operator" refer to a person who has learned how to program instructions into the software that runs the machine, and how to run such a machine and keep it supplied with fabric and threads).

Melco's AMAYA system has become a standardized and widely-used system; however, it is not the only computer-controlled stitching machine that is known and available. Other computer-controlled stitching machines suited for home use have been developed by companies such as Pfaff, Bernina, Singer, etc., all of which have recognized that new and useful functionalities can be created, when people who work out of their homes are able to couple devices such as standard sewing machines, to home computers; in addition, much larger systems have been developed that are suited for use in factories.

Accordingly, the AMAYA system can be regarded as creating and occupying a midpoint, halfway between (i) a low-cost home system that can be created by coupling a standard home-type sewing machine to a home computer, and (ii) a large and expensive factory system. The AMAYA system is well suited for the purposes disclosed herein, and it has been used with very good results; however, any other type, brand, or model of computerized or robotic stitching machine can be evaluated, to determine whether it can be adapted for use as disclosed herein.

It also should be noted that terms such as computerized, computer-controlled, and programmable are used interchangeably herein, and refer to any system that can be controlled by a set of electronic instructions that can be entered into the control system by a trained operator. Such control systems include conventional computers, usually referred to by terms such as mainframe, server, desktop, laptop, or notebook computers. If desired, control systems that can operate computerized stitching machines also can use various types of smaller computerized devices, often referred to by terms such as "personal digital assistants" (including Blackberry, Palm Pilot, Treo, and similar systems), mini-computers, tablet computers, etc., all of which usually are provided with an interface system (called a "universal serial bus", abbreviated as USB) that is designed to enable such units to interact with larger computers.

As yet another option, computerized control systems can use electronic devices that are often referred to as "dedicated" control systems. One class of "dedicated" control systems involves relatively small box-type devices, which are coupled to the machine that is being controlled, by one or more data cables. These types of "small box" control systems usually are provided with a touch-screen, keypad, readout panel, or similar components to enable data display and command inputs. One or more integrated circuits (IC's) are provided inside the box, and these typically are provided with specialized instruction sets, often written in proprietary computer code that is "burned" or otherwise loaded into one or more of the integrated circuits. Other types of "dedicated" control systems are physically mounted on or embedded within a larger machine, as part of the machine; this class of control devices is exemplified by the types of control panels that typically appear in photocopy machines, to allow users to control the number of copies, enlargement and collating options, exposure settings, etc. All of these types of electronic control systems, designed to receive and handle instruction sets that are input into the control system by a human operator, are well-known to those skilled in those particular arts.

Accordingly, the AMAYA machine offers a good example of a computer-controlled stitching machine that was never previously used for the type of use described herein, but which contains a sophisticated computerized control system that provides an operator with a good, flexible, and highly useful range of controllable operating parameters, which can be adapted for use as described herein.

When this type of machine is in use, a piece of backing material that is to be stitched (such as, for example, the chest area of a tennis shirt, the end of a towel, the corner of a handkerchief or scarf, the front of a baseball cap, etc.) is placed in a clamping and stretching mechanism. This mechanism draws the backing layer somewhat taut, in a manner comparable to a miniaturized, movable loom, but usually without stretching the backing layer to an extent that would cause distortion of an embroidered item, after the tension is released and the embroidered item is removed from the machine. The clamping mechanism can then rapidly move the backing layer in any horizontal direction, in a way that is controlled by software instructions that have been entered into the software that runs the machine.

A single sewing needle, which typically points downward, held by a reciprocating mechanism that moves only vertically when in use, is positioned above the backing material. The needle holder (and a threaded needle) move up and down. Each downward stroke causes the tip of the needle (carrying a strand of thread that has been inserted through the eye of the needle) to penetrate the piece of backing material. The backing material cannot be moved, during the portion of the cycle that continues for as long as the needle penetrates the backing material and remains engaged in it. The needle is then raised, disengaging the needle from the backing material while leaving a portion of the thread passing through the backing layer. The backing material is then moved to a new position by the holding mechanism, and the process is repeated, to create another stitch.

The loops of thread that are pushed down through the backing layer, by the needle, can be secured by any of several means. In one approach, often referred to as "interlock" stitching (which creates a type of structure illustrated in cross-section, in FIG. 1), a secondary fiber strand is used, which remains on the back side (or the bottom side, reverse side, underside, etc.) of the backing layer. In this method, an initial enlarged loop is created beneath the backing layer, from the primary stitching thread. A small spool-type device, called a bobbin, is passed through the temporarily-enlarged loop, by a mechanism that transfers the bobbin from a first holder to a second holder (this is sometimes called a "floating" bobbin system). The needle is raised, disengaging it from the backing layer, and the primary stitching thread is pulled tight, in a way that collapses the loop of thread and pulls it snugly around the "locking" fiber, which remains beneath the backing layer. The backing layer is then moved slightly, and the next stitch is created by repeating the same sequence steps, except that the bobbin is transferred back from the second holder, to the first holder; the bobbin simply reciprocates back and forth, between its two different holders, as additional stitches are created.

Other types of stitching use different methods to secure the stitches to a backing layer. For example, a small loop of secondary fiber that will remain entirely beneath the backing layer can be passed through each loop of the primary thread that is pushed downward (by a needle) through the backing layer. The primary thread is then pulled tight, in a way that tightens and secures it against the small secondary loop, beneath the backing layer. In this manner, a relatively simple threaded needle system that remains beneath the backing layer (rather than a more complex "floating bobbin" system) can be used to create the small secondary loops that will prevent the main stitches from unraveling. This approach also avoids the need to make initial loops, beneath the backing layer, that are large enough to pass a bobbin through.

In still other systems, no secondary fibers are used to secure the stitches to the backing layer. Instead, if a moderately thick thread having a significant degree of stiffness is used, the rounded "head" of each loop of thread will remain lodged in the backing layer, each time the needle is withdrawn from the backing layer. Subsequently, after the stitching operation has been completed but before the item runs a risk of being snagged, unraveled, or otherwise damaged, a layer of adhesive can be applied to the bottom side of the backing layer. When the adhesive cures and hardens, it will lock the stitches in place. This approach is used in tufted carpets, embroidered patches, and various other items.

As mentioned above, the backing layer cannot be moved, during each instant when a threaded needle (which can only move vertically, when in operation) has been pushed downward in a way that engages the backing layer. In some types of 3D fiber arrays, a substantial loop of material is created and allowed to remain on the bottom side of the backing layer. 3D fiber arrays created in this manner usually are called tufted arrays, to distinguish them from other types of stitched arrays that are called sewn arrays.

In most types of tufted materials, the "face" side of the material (i.e., the side of the material that will be exposed and visible during normal use, such as in a tufted carpet, once the carpet has been installed on a floor) will be created on the bottom side of the backing layer, during the stitching operation. When a tufting material is being manufactured, loop-grabbing mechanisms (usually called "loopers") are often used to grab the tip of each loop, as each tuft or loop is being formed on the bottom side of the backing layer.

This type of manufacturing process can help ensure uniform tuft heights, as illustrated by the uniform thicknesses of tufted carpets that cover very wide areas. If other types of curved, looping, or other stitch designs are used, in which the stitches are not pulled tight, a mechanical device called the "presser foot" on an AMAYA machine can be adjusted, in ways that will create non-tightened but relatively uniform stitch lengths and/or heights. That device as adjusted by turning a rotatable wheel, rather than via a computer command.

Because of how tufted 3D fiber arrays are manufactured, the majority of the thread mass, in a tufted array, will be located on the side of the backing layer which the threaded needles could reach, only when they penetrated through the backing layer. Accordingly, since AMAYA and most other types of stitching machines use needle holders that are positioned above the backing layers, the tufted loops will be created on the bottom side of the backing layer, during the tufting operation. Subsequently, after the stitching operation has been completed, the stitched layer of material is removed from the machine, and it is then turned over, to position the tufted side (often called the "face" side) on the top side of the layer of material.

By contrast, in sewn 3D fiber arrays, the majority of the thread mass will be on the top side of the backing layer, and only relatively small loops of thread will be created on the bottom side.

In a tufted structure, in each and every tufting loop, the entry point (i.e., where a strand of thread is pushed downward through the backing layer, presuming that the needle holder is positioned above the fabric holder) and the exit point (i.e., where the loop of thread is pulled back upward, through the backing layer) must be at exactly the same location. The entry and exit points cannot be separated by even a single strand of fiber in the backing layer. This arises as an inevitable result of the way tufting loops are created. When a threaded needle is pushed through the backing layer (in a downward stroke, when an AMAYA or similar machine is used), the needle "engages" the backing layer. This means that the shaft of the needle effectively "locks" the backing layer in place for an instant, for as long as the needle shaft continues to engage the backing layer. When the needle is then raised, the thread being carried by the needle will necessarily pass through the backing layer in the same location where it entered. Because of how the needle engages the backing layer, there is no way for even a single fiber of the backing layer to somehow jump across the needle, from one side of the needle to the other side, while a single tufting loop is being formed by a single down-and-then-up stroke of the needle.

Subsequently, after the needle tip has been raised high enough to disengage it from the backing layer, the backing layer can then be moved again, and the next tuft can be created. However, that does not change a crucial fact about tufted structures: in a tufted material, the entry and exit points for any specific tuft must be in the same location, and cannot be separated by even a single fiber of the backing layer.

By contrast, in a sewn 3D array, the "frame of reference" is changed, in a way that causes the "entry" and "exit" points for each stitch to be defined differently. If the needle holder is positioned above the backing layer, then the "face" side of a sewn fiber array will be created on the top side of the backing layer (this is the opposite of tufted materials). Therefore, the "entry" point for each stitch is deemed to be the point where the stitching thread rises up through the backing layer, and begins its travel path across the important side (i.e., the face side, functional side, etc.) of the embroidered or otherwise sewn material that is being created. Accordingly, the "exit" point for any given stitch is the location where the stitch then travels back down through the backing layer, in a way that effectively removes the thread from the face side of the material. If desired, any single stitch can be caused to form a closed loop, in which the entry point and exit point will be the same. However, in most cases, there is no reason to do that, and instead, the backing layer will be moved slightly, each time the needle is raised above (and disengaged from) the backing layer. This will cause each stitch to travel (or "traverse") at least some distance across the surface of the backing layer. Accordingly, as noted above, in a sewn 3D fiber array, the majority of the thread mass will be formed on the top side of the backing layer, and only relatively small closed loops of thread will be positioned on the bottom side. Because of how the needle engages the fabric during each downward stroke, the small loops of thread on the bottom side of the backing layer must have exactly the same entry and exit points, which cannot be separated by any strands of fiber in the backing layer, even if an "interlocking" thread is inserted through each loop by means of a floating bobbin.

The AMAYA system (and most other computer-controlled stitching machines that are not designed to be "dedicated" to only a certain specific and limited type of manufacturing operation) can be programmed to make either sewn or tufted 3D fiber arrays, by changing the control parameters for any particular prototype (or any "production run" that will make two or more copies of items having identical designs).

The AMAYA system also provides an entire set of spool-holders, which can provide different colors and types of threads to a set of needles. Only a single needle will be active at any time; however, sixteen different needle holders are provided in a typical AMAYA unit, and each needle can have its own supply of thread, from a dedicated spool. This was designed to enable multi-colored embroidery, using up to 16 different colors or thread types, and when it is time to change from one color to another, the machine can do so automatically, based on an instruction set programmed into the computer before the stitching operation commenced.

Entering a set of instructions that will control a prototype or production run is comparable to writing a document on word processing software, or filling in boxes on spreadsheet software. Word processing or spreadsheet software can provide options and guidance, but it will not control what is typed onto any pages, or entered into any blanks or slots. In the same way that anyone who learns to use a word processing program can write anything they want, anyone who learns to use the software that controls a stitching machine can use it to create embroidered depictions of anything they want (such as animals, spaceships, or team mascots, as just a few examples). To do this, the creator can take any of several approaches, which include: (i) creating a graphical drawing of such an item, using tools that are provided by any of various types of drawing programs; (ii) scanning a photograph of such an object, and digitally converting the scanned image into an instruction set that will create a similar image using colored threads on a backing layer; or, (iii) buying a "clipart" instruction set from a person or company that creates and sells images that have been drawn by artists and then converted into instruction sets designed for use in computerized stitching machines.

Online help, customer support technicians, and user support groups for AMAYA users are all available, via the Internet. Training materials and courses, and instruction books and videos, also are available for anyone who wants or needs to learn to use these types of machines. These are not described in detail herein, because they are readily available elsewhere. Anyone who learns to work such a machine will learn how to control and vary each of a number of different parameters, including fill density, fill stitch length, primary underlay density and stitch length, secondary underlay density and stitch length, primary underlay angle, speed (in stitches per minute), and run fill/feed. If an operator understands those parameters, and understands how the products that result are affected, when those parameters are modified, he or she can create stitched segments having the shapes of circles, ovals, polygons, wedges, arcs, etc., and having loops or stitches with controllable heights, densities, and other parameters, using combinations of (i) any selected type of suitable backing layer, and (ii) any selected type of fiber(s) having any desired combination of chemical content, thickness, stiffness, and other traits.

Computer-controlled stitching machines have been used previously to create various types of surgical implants; however, to the best of the knowledge and belief of the inventors herein, none of those implants or reinforcing materials have ever previously been designed or used to reinforce hydrogel materials, in implants designed to repair hyaline cartilage in mammalian joints.

For example, various types of "surgical mesh" are used in implants that do not contain hydrogels. Such materials are sold by companies such as Secant Medical (www.secant.com), and Dupuy Mitek (a subsidiary of Johnson & Johnson, which can be accessed through www.jnjgateway.com). However, those types of meshes tend to be relatively thin and flat materials with loose and open structures, and they are not suited for use as described herein.

Other types of porous fabrics called "velours" are used in surgical implants, to create fiber arrays that will encourage cells to grow into the fabric after implantation. For example, velour materials made of a combination of biodegradable polymers (such as polyglycolic acid) mixed with collagen fibers (usually obtained from processed cowhide) are used for blood vessel grafts. These implants encourage ingrowth by endothelial cells, which then secrete enzymes that gradually dissolve and resorb the velour material, while the cells replace the fibrous scaffolding with normal collagen protein, to create regenerated blood vessel tissue. These types of vascular grafts are made and sold by companies such as Boston Scientific. However, those types of velour materials are not suited for use in the types of implants described herein, which have very different structural and operating requirements.

Specialty companies (such as Ellis Developments, Ltd., which describes and illustrates its products at its website, www.ellisdev.co.uk) have developed various types of embroidered implant devices, for purposes such as reconstructive shoulder surgery, hernia repairs, etc. Using a method that was initially developed to create doilies and other items that have an "open" look, these implants are created by using a "base fabric" that can be dissolved and removed after a stitching operation has been completed. For example, by using a backing layer made of a paper-like cellulose derivative (or some other material with a chemical structure different from the threads that create the stitches), it is possible to use detergents, solvents, or hot water to remove the base material, leaving behind an embroidered item with any desired two-dimensional shape. These and other types of thin and flat surgical implants are described and illustrated in McQuaid 2004, U.S. Pat. No. 6,899,728 (Phillips et al 2005), and PCT application WO99/37242 (Phillips et al).

Embroidered and other textiles that have been developed and tested for various medical uses are reviewed in items such as Karamuk et al 2000, McQuaid 2004, and Ellis 2000, and companies that specialize in designing and creating such textiles include Ellis Developments (www.ellisdev.co.uk) and Sew Fine LLC (www.alsew.com).

However, to the best of the inventors' knowledge and belief, none of the items created previously for other medical purposes (such as blood vessel grafts, tendon or ligament repair, etc.) are suited for creating 3D fiber arrays that will have the types of relatively open structures with consistent thickness that will be needed for optimal reinforcement of hydrogel layers, in implants designed to replace the relatively thin hyaline cartilage layers that cover certain bone surfaces.

In addition, to the best of the knowledge and belief of the inventors herein, none of the stitched implant devices created in the prior art have been created in ways that are designed to enable such implants to be securely anchored to hard bone surfaces that may be subjected to thousands or even millions of cycles of compressive and shearing stresses, when used to replace hyaline cartilage in a knee or other joint.

Accordingly, one object of this invention is to disclose that certain types of stitched structures, adapted from textile embroidering, carpet tufting, and similar manufacturing methods, can be adapted to provide 3D fiber arrays that are well-suited for reinforcing hydrogel implants for replacing hyaline cartilage.

Another object of this invention is to disclose that certain types of computer-controlled machines, initially developed to manufacture tufted or sewn materials, can be adapted to provide stitched 3D fiber arrays that can strongly and efficiently reinforce hydrogel implants designed to repair hyaline cartilage.

Another object of this invention is to disclose that computer-controlled stitching machines are ideally suited for creating low-cost reinforced hydrogel samples and prototypes that can be tested in an escalating series of in vitro tests, animal tests, and human clinical trials, during the development and optimization of stitching patterns and parameters that can provide optimal reinforcement for the hydrogel components of implants for replacing hyaline cartilage.

Another object of this invention is to disclose surgical implants having hydrogel components reinforced by stitched 3D fiber arrays, in structures that are well-suited for strong and permanent anchoring to hard bone surfaces in joints that are subjected to high loadings and stresses, such as knees.

Another object of this invention is to disclose flexible surgical implants having reinforced hydrogel components that are designed to replace entire segments of relatively thin hyaline cartilage, rather than merely providing plug-type inserts that will create articulating surfaces that have undesired gaps, crevices, and other discontinuities that are likely to cause abrasion over a span of years.

Another object of this invention is to disclose methods for shaping the upper ends of tufting or pile fibers that reinforce a hydrogel material, and that emerge from a backing layer in a perpendicular orientation, into an alignment that is parallel with (and tangential to) a hydrogel surface in a surgical implant.

These and other objects of the invention will become more apparent through the summary, drawings, and detailed description.

SUMMARY OF THE INVENTION

Surgical implants for replacing hyaline cartilage in mammalian joints are disclosed, containing a hydrogel layer reinforced by a three-dimensional (3D) fiber array. It is preferred that such implants be sized to replace entire segments of cartilage (such as a medial femoral runner or tibial plateau, or a lateral femoral runner or tibial plateau), in a way that replaces an entire articulating surface, rather than inserting a plug into damaged cartilage in a way that would create a crevice or other surface discontinuity surrounding the plug. To replace entire segments of hyaline cartilage, the implants disclosed herein must be relatively thin and flat, and must cover a larger area than a plug would cover. Both the hydrogel polymer and the reinforcing fiber array must be flexible, to allow the implant to be rolled into a cylinder that can be inserted arthroscopically into a joint.

Preferred methods for created optimal 3D fiber arrays can use computer-programmable stitching machines. Such machines can add large numbers of tufted loops or sewn stitches to a backing layer such as a flat woven fabric. When used as described herein, computer-controlled stitching machines enable a single copy (or any desired number of copies) of a redesigned implant to be fabricated, having one or more new parameters that have been modified based on earlier test results, with little or no delay and with no "fixed cost" or "overhead" requirements. Accordingly, adapting such machines to this type of work provides researchers and companies with greatly improved tools and options for the testing and optimization that must be completed before any such implants can be finally approved for sale and use as medical or veterinary devices.

To preserve a hydrogel's permeability to water, reinforcing fiber densities should be less than about 50%, and in most cases likely will be less than 30%, when measured as a fraction of a horizontal cross-section through the center of a hydrogel layer. In addition, care must be taken to ensure that the tips of any tufts or stitches do not reach and disrupt the smooth exposed surface of a hydrogel layer, which will become an articulating surface after surgical implantation of the device. Methods also are described to become parallel (tangential) to the surface, in case such steps are shown by testing to to minimize any risks of abrasion over a span of years or decades of use.

The opposing side of an implant must be suited for anchoring to a bone surface from which the native cartilage has been removed, and it preferably should be made of a porous material that will encourage tissue ingrowth into the implant. Methods and structures also are described for affixing a reinforcing 3D fiber array to a rim component made of a nitinol alloy or shape-memory material, for secure anchoring of such implants (which in many cases will have curving, rounded shapes) to hard bones.

DETAILED DESCRIPTION

Figure 1:
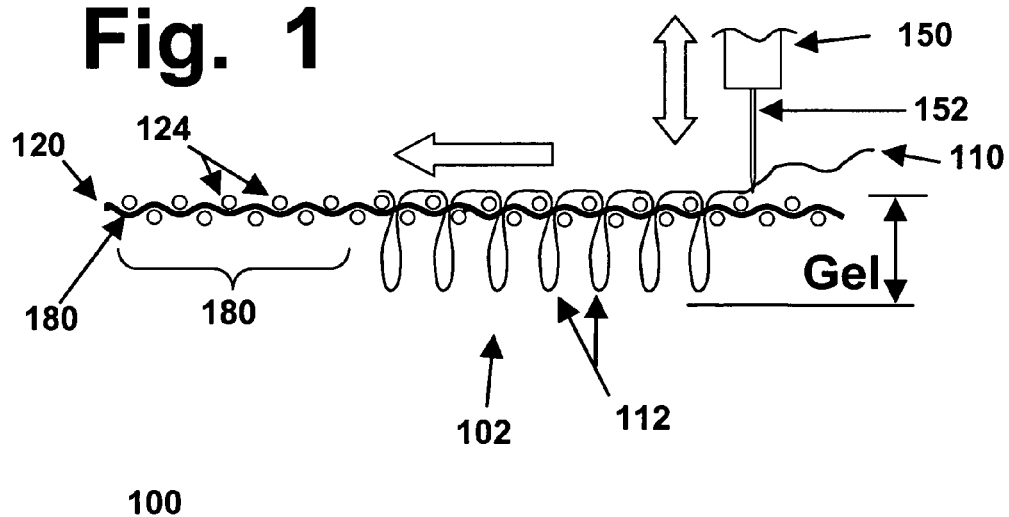
FIG. 1 is a cross-sectional depiction of a hydrogel-reinforcing fiber array with stitches being created in a tufted manner, with the tufts on the opposite side of the backing layer than the needle holder. The backing layer has an unstitched margin around its periphery, to allow ultrasonic welding of the backing layer to a polymer component in an anchoring device.

As summarized above, three-dimensional (3D) fiber arrays are disclosed, for reinforcing hydrogel layers in relatively thin and flexible surgical implants for replacing hyaline cartilage in mammalian joints. The reinforcing layers and implants disclosed herein can be manufactured in any desired widths and lengths, and can enable the replacement of entire segments of hyaline cartilage, rather than merely creating plug-type implants that will create gaps and discontinuities in a repaired cartilage surface. However, despite their relatively large surface areas, these implants can be thin enough to render them flexible, for insertion into a joint using arthroscopic methods and devices.

If a suitable fabrication method is used to make the reinforcing layers (such as by using a computer-controlled stitching machine, as described below), these types of hydrogel implants can be made in ways that render them well-suited for: (i) permanent bonding to an anchoring rim, which can be made of a strong material such as a nitinol-type alloy; and, (ii) providing a porous layer on the anchoring surface that will promote tissue growth into the porous layer, to create stronger and more durable anchoring of the implant to a bone surface.

For convenience and clarity, all discussion below assumes that the computer-controlled stitching machine being used to create a 3D fiber array for reinforcing a hydrogel layer in an implant as described herein will have two principle operating components: (1) a single threaded needle that is active at a given time, and that is able to travel only vertically, while active; and, (2) a fabric-holding device that can stretch and hold a piece of fabric (or other sheet-like backing material) in a relatively taut horizontal position while stitches are being created on the backing layer, and that also is designed to be able to move the sheet or segment of backing material in any horizontal direction that has been programmed into the software that control the machine. This discussion assumes that the needle-holder is positioned above the backing holder, thereby causing the tip and shaft of the needle to: (i) penetrate through (and thereby engage) the backing layer, during the downward portion of each needle stroke; and, (ii) rise above (and thereby disengage from) the backing layer, during the upward portion of the needle stroke. Downward movement of the needle during each stroke or cycle, and/or the moments when the needle penetrates and engages the backing layer, can be referred to as extension, thrust, lowering, engagement, or similar terms. Upward travel of the needle, and/or the state of disengagement of the needle from the backing layer, can be referred to as retraction, withdrawal, raising, disengagement, or similar terms.

As described in the Background section, and because of how these types of stitching machines operate, the types of stitching that are of interest herein can be grouped into two main categories, which are tufted and sewn.

As illustrated in FIG. 1, a tufted 3D array 100 is created when thread 110 is pushed through a backing layer 120 (which is shown as strand 122, interlaced between the cross-sectional ends of strands 124), in a manner that creates and preserves elongated loops 112. In a machine where the needle holder 150 and needle 152 are positioned above the backing layer 120, this initially will create tufts that point downward; after the stitching operation has been completed, the resulting tufted material normally will be turned over, so that the tufted side 102 (often called the face side, finished side, or similar terms) will be on top, during subsequent processing.

The vertical arrow next to the needle holder 150 and threaded needle 152 indicates that those devices will move only vertically, when in use. The horizontal arrow above the backing layer indicates that it will be pulled slightly to the left, each time the tip of needle 152 rises high enough to disengage from the backing layer 120, when creating that row of tufted loops. Multiple rows of tufting loops will be created, with each row having dozens, hundreds, or even thousands of miniaturized tufts, to create a fiber array that will have a moderate but not excessive "areal density", as described below.

As mentioned in the Background section, two practical results arise from how tufted loops are formed. First: most of the thread mass and weight will be positioned on the side of the backing layer that is positioned away from the needle holder. Second: the entry and exit points for any tufted loop must be immediately adjacent to each other, and cannot be separated by even a single fiber of backing layer 120.

The "length" of the tufts will become the tufting height, after the stitching operation has been completed, and the material is removed from the machine and turned over, so that the tufts point upward. This dimension, which is perpendicular to the backing layer 120, might also be referred to as the thickness of the 3D fiber array; however, since a hydrogel layer subsequently will increase the thickness of the final device, use of the term "thickness" might be confusing, if applied to only the tufted layer that will be embedded inside the hydrogel. Therefore, "tufting height" is preferred, when referring to a tufted 3D array without a hydrogel layer affixed to it.

Tufting height can be determined relative to any of three "baseline" or starting point levels, which are: (i) the top surface of the backing layer; (ii) the centerline of the backing layer; or (iii) the bottom surface of the fiber array, including the backing layer. Since it is convenient to measure the thickness of an entire fiber array, without having to discount the thickness of the backing layer, tufting heights preferably should refer to the thickness of an entire tufted fiber array, including the backing layer and any additional thickness imparted by the small loops of material on the "bottom side" of the array.

The hydrogel normally will not be affixed to the fiber array until after the fiber array has been removed from the stitching machine. As implied by FIG. 1, the hydrogel layer should be thick enough to prevent any fiber strands or loop tips from being exposed on the articulating surface of the hydrogel, since any fiber strands exposed on that smooth surface could create unwanted abrasion by the implant, after surgery.

Unlike a tufted carpet, in which the tufts are packed together tightly, to provide resistance and resilience against the weight of people walking repeatedly on the carpet, the tufts in a 3D fiber array that reinforces a hydrogel do not need to be packed tightly together, since they generally will need to provide only tensile strength, to prevent the hydrogel from being torn. The hydrogel itself, if made of a sufficiently strong polymer, will provide all necessary compressive strength and resistance. Therefore, the tufts generally should have a limited and somewhat loose "areal" density (such as less than about 50%), to prevent air or gas bubbles from being trapped in the fiber array when the hydrogel material is being added and affixed to the fiber array, and to help sustain the permeability of the hydrogel to water, after implantation of the device.

Areal density can be expressed as the fraction (or percentage) of a horizontal cross-sectional area of a hydrogel material containing a fiber reinforcing array, measured at or near the middle of the height of the fiber array. Unless and until data from in vitro tests of prototype samples indicate otherwise, it is believed that areal densities ranging from about 5% to about 50% can provide sufficient reinforcement without seriously impeding water travel through fiber-reinforced hydrogel materials, and areal densities of about 10 to 30% offer preferred candidates for early evaluation. The preferred density for any particular fiber-reinforced hydrogel will depend on various factors, such as whether monofilaments or yarns are used, the thicknesses of the strands of fiber or yarn, and the intended location for a particular implant (for example, implants for finger joints are likely to require less reinforcement than implants for knee joints).

It also should be recognized that the tufting height (or other measures of the thickness, height, or depth of a 3D fiber array) does not need to reach any particular fraction or percentage of a hydrogel thickness, for all implants. Depending on factors such as the strength and toughness of a hydrogel polymer, the type of joint an implant will be used to repair, and the size and dimensions of the implant, some implants that are intended to repair loaded joints (such as knee joints) may be strongest and most durable, if their reinforcing 3D fiber arrays extend through 90% or more of the thickness of the hydrogel layer. By contrast, other implants that will subjected to lower loadings and stresses (such as in finger joints) may have sufficient reinforcement, so long as their 3D fiber arrays merely provide an adequate transition zone between a backing layer or anchoring component, and a softer hydrogel. Transition zones in such implants might occupy, for example, only about 10% to about 30% of the thickness of the hydrogel layer.

Finally, FIG. 1 also indicated a "margin" area 180, where backing layer 120 does not have any tufts or stitches. This margin area, which generally will extend around the periphery of a segment of tufted (or sewn) material, is designed to allow subsequent handling and processing of a stitched fiber array, in ways that would be rendered impractical or more difficult, if stitching covered the margins. For example, as discussed below, the presence of unstitched margins around the periphery of a fiber array can allow ultrasonic welding of the backing layer to a polymer component that is gripped and held by a "shape-memory" material (such as a nitinol alloy) that is part of an anchoring rim.

Figure 2:
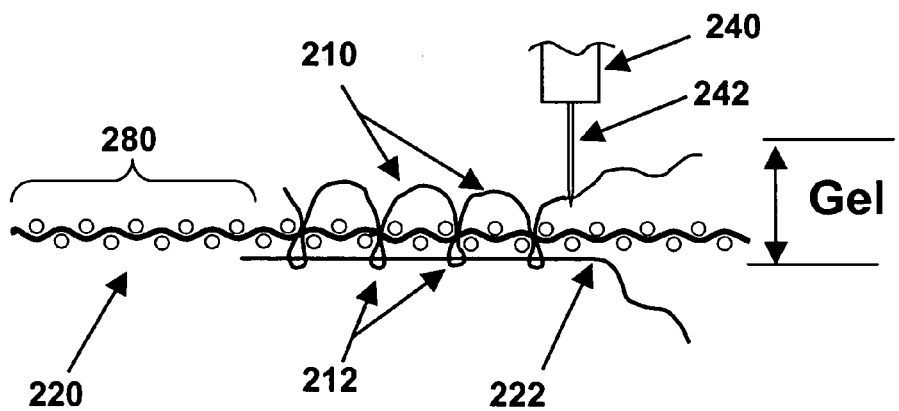
FIG. 2 is a cross-sectional depiction of a hydrogel-reinforcing fiber array with sewn stitches being created on its top side (i.e., on the same side of the backing layer as the needle holder). The stitches are held in place by an interlocking fiber beneath the backing layer, and the backing layer has an unstitched margin around its periphery.

FIG. 2 illustrates a sewn 3D fiber array 200, having stitches 210 with their longest portions on the same side of backing layer 220 as needle holder 240 and needle 242. Only small loops 212 are positioned below backing layer 220, and FIG. 2 illustrates an "interlocked" stitching structure, in which a locking fiber 222 is passed through each loop 212, by means of a "floating bobbin" mechanism, before the loop 212 is pulled tight against the locking fiber. As illustrated in FIG. 2, each sewn stitch 210 usually will traverse some distance across backing layer 220, with the entry point and exit point for a stitch separated by at least one fiber in the backing layer 220. Since the longer stitch portions 210 are above the backing layer while the short locking loops 212 are below the backing layer, most of the thread mass and weight will be created on the same side of the backing layer as the needle holder 240. FIG. 2 also shows an unstitched margin around the periphery of the sewn fiber array, to enable attachment of the fiber array to another implant component, such as ultrasonic welding attachment to a polymer component in a nitinol anchoring rim.

Tufted 3D arrays may be able to provide greater consistency, uniformity and control over thickness, than sewn fiber arrays in which the stitches are not pulled tight and have substantial surplus length. This is especially true if a stitching machine that is being used to create tufts uses a "looper" device to momentarily grab the tip of each tufting loop, as it is being created, and it should be noted that the AMAYA machine does not have or use such "looper" devices. However, alternate means can be used to create sewn stitches with relatively consistent "heights" above a backing layer. For example, on an AMAYA machine, an adjustable mechanical wheel (which is not directly controllable by any software, coding, or similar instructions, but which can be readily accessed and manipulated by an operator) can be used to vary the setting of a device called the "presser foot" during a stitching operation. A higher presser foot setting will create stitches that have taller heights, in a consistent manner.

If testing (using microscopic analysis and photography, in a manner comparable to histological examination of cells and tissues) indicates that additional steps must be taken to prevent any tufting loops or sewn stitches from reaching and disrupting the smooth articulating surface of a hydrogel layer, such steps can be taken. For example, a layer of mesh or screen material can be placed over the outer surface of a set of tufted or sewn stitches; alternately, if thicker fibers with greater stiffness are used, they are likely to establish curves and arcs that have greater consistency and less variability, compared to thinner and more flexible fibers. It should also be noted that if a 3D fiber array rises to only a limited and partial height (such as less than about 80% of the thickness of the hydrogel layer), the risk of protruding stitches disrupting a smooth surface may be minimal or nonexistent.

It also should be kept in mind that the types of fabrics usually known as felt, velour, and chenille offer additional examples of fabric types where loop or stitch length and height must be kept consistent. Accordingly, if variations in loop or stitch length and height, in 3D reinforcing arrays as described herein, create problems of unwanted variability that jeopardize quality control, the methods and machines used to create those three other classes of fabrics can be studied and evaluated in detail, to determine whether such methods and/or machines can be adapted for use in reducing any such unwanted variability and other problems.

A hydrogel polymer can be affixed to a 3D fiber array, by means of a molding and curing process that uses a liquid referred to herein as a "prepolymer". Various means are known for converting liquid prepolymers into cured, solid but gelatinous polymers; for example, polyacrylonitrile polymers are often cured by heating a homogenous liquid to a reaction temperature, and then allowing the polymer to cool again, while polyurethane polymers are often created by mixing a resin with a catalyst, and then allowing the two liquids to chemically react with each other.

Normally, to help ensure a smooth and flat top surface, a liquid prepolymer will be poured or otherwise distributed on top of a 3D fiber array that is resting in a tray or similar holder; alternately, it is possible to use methods that involve dipping a fiber array into a tray that holds a liquid prepolymer. If desired, a vibrating or impact-generating support device, sonic waves, a raking or combing device, a roller or other compressor device, or other means can be used to help dislodge and remove any air bubbles that may initially be trapped beneath the liquid surface, after a prepolymer liquid has been poured on top of the fiber array.

The shape and size of a backing layer used to create any particular type of implant also can be controlled and varied by methods known to those skilled in the art, such as by using a fabric or plastic backing layer that was created with (or subsequently given) a curvature or other "bias". In this manner, implants having controlled shapes can be created for different types of joints, and for patients of different sizes. As examples, stitched 3D fiber arrays as described herein can be sized and shaped in ways that will accommodate entire unicompartmental segments of femoral runners, tibial plateaus, or patellar surfaces in knee joints, ball or socket surfaces in hips or shoulders, knuckle joints in fingers or toes, or any other articulating joint surfaces that may need repair, in people suffering from injuries, arthritis, or other disorders, and they can also be creating with smaller sizes, if desired, to serve as plug-type implants that will be stronger and more durable (and that can be anchored more securely) that other types of plug-type implants available today, such as SALU-CARTILAGE implants, described in the Background section. Orthopedic manufacturing companies are already very familiar with the sizes and shapes of implants that are needed for the various joints of the body that commonly need repair, and the exact size of any targeted bone surface in any patient can be readily determined by X-rays or other medical imaging methods before surgery begins, when time is available to order and receive an implant that will be optimally sized and shaped for that individual patient.

Securing 3D Fiber Arrays to Anchoring Rims

As mentioned above, if a cartilage-replacing implant is not specifically designed to be dissolved and resorbed by the body, the reinforcing fiber array should be made of nonresorbable synthetic polymers. Candidate polymers include polyesters, high (or ultra-high) molecular weight polyethylene, polycarbonate urethane, polyacrylonitrile, and others that are known to those skilled in the art. Numerous companies (such as Secant, Putnam Plastics, the Depuy-Mitek division of Johnson & Johnson, etc.) sell synthetic sutures, and researchers, technical support specialists, and vendors at such companies are experts in the performance traits and comparatives advantages and disadvantages of such materials for various surgical uses.

In at least some cases, a design requirement is likely to result in selection of one type of polymer for the backing layer, and a different type of polymer for the stitches. This trait arises from the need to be able to securely and permanently affix the 3D fiber array that will reinforce a hydrogel polymer, to an implant component referred to herein as an anchoring member. When used with implants for replacing hyaline cartilage, the anchoring member normally will be used to help securely affix the implant to a hard bone surface from which the native cartilage has been removed.

Examples of such anchoring devices, specifically designed to securely anchor cartilage-replacing hydrogel implants to prepared bone surfaces, are discussed in more detail in Patent Cooperation Treaty patent application PCT/US05/43444, by Mansmann et al, filed in November 2005. That PCT application claims priority based on U.S. provisional applications 60/631,652 (filed in November 2004), 60/656,606 (filed in February 2005), and 60/685,345 (filed in May 2005), and it is scheduled to be published in about May 2006. The contents and teachings of that PCT application, and of all three provisional applications listed above, are incorporated herein by reference, as though fully set forth herein.

Briefly, those patent applications describe the design and use of anchoring rims that are attached to anchoring pegs (or studs, posts, or similar terms). During a surgical procedure, the anchoring pegs will be pressed into eternally-threaded barrels (or sleeves, cylinders, etc.), which will be emplaced and secured in holes that are drilled into a prepared bone surface. In order to provide the surgeon with room to work and maneuver, the holes will be drilled into the bone, and the anchoring barrels will be positioned and secured in the drilled holes, before the body of the implant device is inserted into the joint.

The rim of this type of anchoring component will comprise a flexible polymer, which can be reinforced if desired by a metallic or other hard component made of a "shape-memory material". These materials grew out of the discovery in the 1930's of an alloy called "nitinol", which shrinks when heated. Other shape-memory materials known today will shrink when chilled; these can allow insertion of temporarily "shrunken" implant devices that have been chilled, in ways that minimize any damage to surrounding tissue during the insertion step. After the chilled implant has been properly positioned, the shape-memory material will be warmed up again, by body tissues and fluids, and it will expand back into its original shape.

If a metallic alloy or comparable shape-memory material forms a rim component or similar structure that will be used to anchor a cartilage-replacing implant to a bone or other tissue, the rim component or similar structure can be provided with an insert (which can also be called an inset, component, member, or similar terms) made of a selected type of polymer.

This polymer insert will need to be an elastomer, to enable it to change shapes as the anchoring device is chilled and shrunk for insertion, then expanding again after insertion, into its normal shape.

Accordingly, in this type of implant, the 3D fiber array must be securely and permanently affixed to the anchoring member (which in most cases will surround the implant device, establishing its periphery).

If suitable materials have been selected for all components involved, this permanent attachment can be created, reliably and without using potentially toxic or leachable chemical adhesives, by means of a process that is usually called "ultrasonic welding". This process uses focused sound waves at a very high frequency, in a manner that can soften, melt, and join two pieces of compatible plastic that are being pressed against each other. Skilled use of this welding method can create the highest local temperatures at a contact zone or interface, where two pieces of plastic are being pressed against each other (this creation of localized heat is analogous to the way unwanted heat is often created at an imperfect electrical connection, when current is forced through the connection).

If ultrasonic welding will be used to permanently affix the 3D fiber array to an anchoring member, then the polymer that is selected and used to make the backing layer of the fiber array should be different than the polymer used to create the stitches. The backing layer, and the "weldable polymer" component of the anchoring member, should be made of a first class of selected polymers that will allow those components to be ultrasonically welded to each other, without affecting the stitches in the 3D fiber array; and, the stitches in the 3D fiber array should be made of a second class of polymers that will not be affected by the ultrasonic welding operation that will be used to affix a backing layer to an anchoring component.

Figure 3:
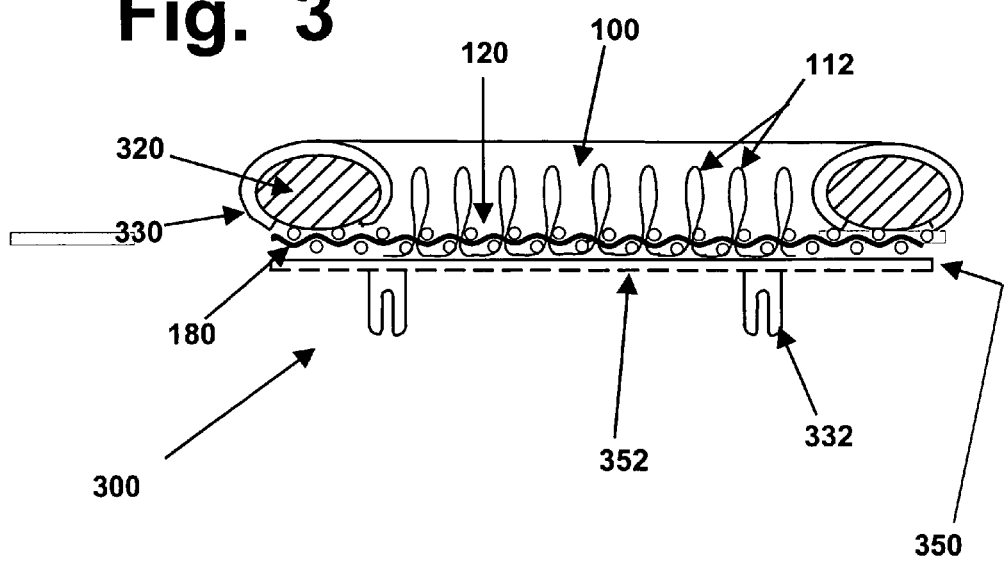
FIG. 3 is a cross-sectional depiction of an implant device with a reinforcing hydrogel layer, affixed to an anchoring rim having: (i) an annular ring made of a nitinol alloy or similar shape-memory material; (ii) a polymer ring, for ultrasonic welding to the polymeris backing fabric of the reinforcing layer; (iii) anchoring pegs, affixed to the nitinol alloy ring; and, (iv) a porous bottom surface, to promote tissue ingrowth.

Accordingly, FIG. 3 depicts an implant assembly 300, shown in a simplified cutaway view, before the hydrogel polymer has been added to the implant. This implant comprises a tufted 3D fiber array 100 as illustrated in FIG. 1, with backing layer 120, tufts 112, and a non-tufted "margin" 180 of backing layer 120 only, around the periphery of backing layer 120. The margin 180 of backing layer 120 has been ultrasonically welded to a compatible polymer ring 320, which is largely enclosed and secured within an annular ring 330, made of a nitinol-class alloy or other suitable shape-memory material. The polymer ring 320 and annular ring 330 are components of a generally circular or oval anchoring ring. A plurality of anchoring pegs 332 (illustrated in more detail in above-cited patent application PCT/US05/43444) also are affixed to the anchoring surface of annular ring 330, at distributed locations.

In most cases, it likely will be preferable to weld the reinforcing fiber array to the anchoring member, before the hydrogel material is affixed to the fiber array. Sequencing the steps in this manner can avoid any risk that the hydrogel might interfere with (or be damaged by) the ultrasonic welding process.

FIG. 3 also shows an optional layer 350, on the anchoring surface of the implant. This optional layer 350 will be impermeable to the prepolymer liquid that will be poured onto the fiber array, to form a reinforced hydrogel. However, it will be designed in any of various known ways that can be used to provide a porous exposed surface 352 on the bottom of the implant, by the time the manufacturing process has been completed. For example, layer 350 can be made of a bilayer material with a nonporous top and a porous bottom; alternately or additionally, some or all of layer 350 can be embedded with particles or fibers made of a substance that can be removed by a finishing step (such as, for example, salt particles that can be dissolved by water and rinsed out, or a nontoxic wax with a low melting temperature). The porous surface on the exposed bottom surface of the implant will encourage tissue ingrowth into that bottom layer, after the surgery has been performed, leading to stronger anchoring of the implant to the bone.

Creating "Biased" Fiber Orientations

Whenever a synthetic device is being designed as a replacement for natural tissue, all aspects of the natural tissue (including its molecular, microscopic, and macroscopic structures, its form, its functions, etc.) should be studied carefully, and kept in mind.

As mentioned in the Background section, and as shown in photographs by electron microscope (published in sources such as Clark et al 1990 and 1991), collagen fibers that establish the structure of natural and healthy hyaline cartilage, in mammals, emerge from the subchondral bone surface in a radial direction (i.e., generally perpendicular to the surface of the bone, at the site where the fibers emerge from the bone). Those fibers go through a rounded transition, to reach a generally tangential orientation at the articulating surface of the cartilage. That tangential arrangement of the fibers, on the surface of the cartilage, helps provide a smooth and nonabrasive surface.

If a synthetic hydrogel reinforced by a 3D fiber array is being created, an important design principle indicates that the reinforcing fibers should not be exposed, at all, on the smooth articulating surface of the hydrogel. However, despite that principle, there may nevertheless be some value in imparting, to a 3D fiber array made by stitching, a "bias" to the tufts or stitches.

The term "bias" is used herein in a structural and mechanical rather than social or political sense; however, the overlap in terms becomes apparent, since the result (in layman's terms) is to create strands that will "lean" in a certain direction. This type of bias can be "fixed" in a way that will render it permanent, for the life of the implant.

Two different types of fiber biases may turn out to be important in this invention, and both can be evaluated using in vitro tests, on a machine, without requiring any animal testing or clinical trials.

One type of bias relates to the directions of any tufted loops or sewn stitches, when considered from a "plan" view, while looking down at the articulating surface of a hydrogel implant. For example, because of how the knees are structured, nearly all of the relative motion between femoral runners and tibial plateaus is in a forward and backward direction (i.e., along the anterior-posterior axis), rather than in a side-to-side direction (along the medial-lateral axis). Therefore, there may be some type of minor and marginal advantage (which may not become apparent until multiple years have passed, after implantation), for tufts or stitches that are oriented mainly in an anterior-posterior direction, for femoral runner or tibial plateau implants. This type of bias can be easily provided, merely by programming a computer-controlled stitching machine to do so. Wear-testing of such implants, both with and without that type of bias, over millions of stress cycles, can then be performed on a tribometer machine.

Figure 4:
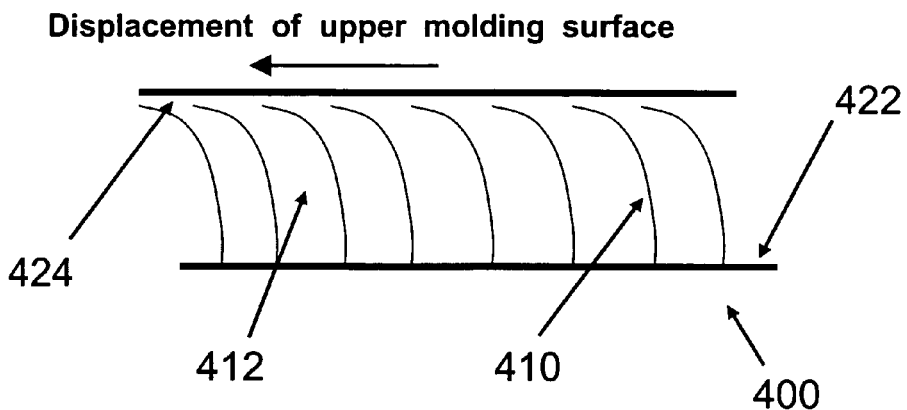
FIG. 4 is a cutaway cross-sectional schematic depicting a shearing-type displacement of two molding surfaces, to give the tufted reinforcing fibers a "bias" that will cause them to lean in a desired direction that approaches tangential orientation near the smooth articulating surface of the hydrogel layer.
Figure 5:
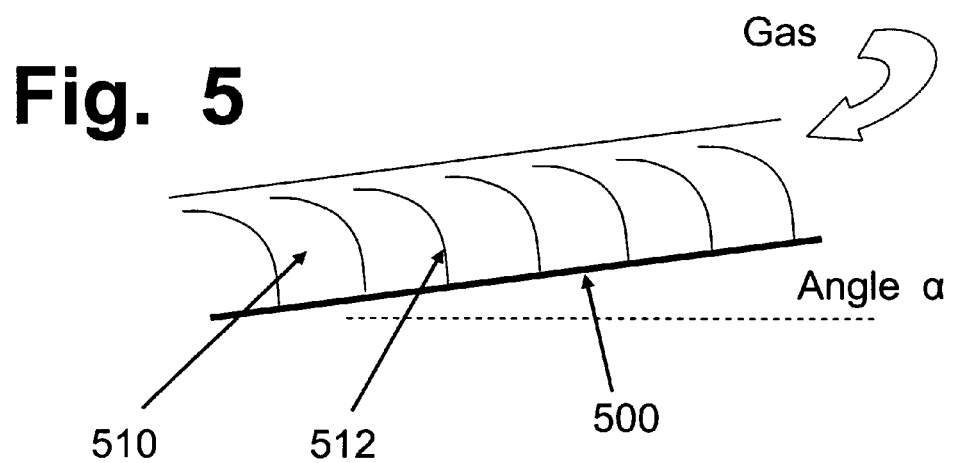
FIG. 5 is a cutaway cross-sectional schematic depicting a molding tray positioned at a sloped angle while an inert gas is being blown across its surface, in a manner that will cause the reinforcing tufts to bend and lean in a tangential direction when a prepolymer liquid is applied to them.

A different type of fiber bias can be visualized by considering a reinforced hydrogel in an "elevation" cutaway view, rather than a plan view. This type of bias, and a method of creating it in reinforcing tufts embedded in a hydrogel, is illustrated in FIGS. 4 and 5. In implant 400, shown in FIG. 4, the synthetic tufts 410 are shown as having a transition from vertical, at their base, to horizontal, near the articulating surface of the hydrogel. This is similar to the rounded transition that the collagen protein fibers in natural cartilage pass through, as they travel from the subchondral transition zone (where they emerge from the bone in an essentially perpendicular or radial direction), to the articulating surface of a hyaline cartilage segment.

This type of biased fiber orientation, to create a transitional structure for strands of synthetic tufts, can be created by any of several approaches. For example, as illustrated by FIG. 4, it can be created by using a shearing-type displacement of a molding device, comprising a lower tray-type supporting surface 422, and an upper molding surface 424. This shearing-type displacement is carried out during a manufacturing step that is normally referred to as curing, setting, hardening, etc., when a pre-polymer liquid 412 is being chemically converted into its final gelatinous polymer form.

Alternately or additionally, a displacement step can be carried out on the tufting strands alone, after the tufting material has been properly positioned in a mold, and before the pre-polymer liquid is loaded into the mold. For example, a combing, rubbing, blowing, or similar operation can be carried out on the tufting material, before the liquid is applied.

As another option, a molding operation can be carried out at an inclined angle, in a way that allows gravity to help create or sustain the desired bias in the tufting strands. As illustrated in FIG. 5, a molding tray 500 is positioned at a sloped or slanted angle (designated as "alpha" in FIG. 1) relative to the horizontal, while a pre-polymer gel-forming liquid 510 is poured over, spread across, or otherwise applied to a set of reinforcing tufts 512 affixed to a backing layer that rests on the tray surface. In some situations, this type of sloped molding operation may eliminate the need for an upper molding surface. Alternately or additionally, this type of sloped arrangement can be used during only a portion of a molding operation, such as during the period when a liquid pre-polymer is initially being poured on top of the tufting material; subsequently, as the liquid begins to cure into a gelatinous polymer, the molding tray can be rotated into a flat horizontal position.

As yet another option, when using some types of polymers, it may be possible to carry out a biasing step by using heat (or possibly some other suitable treatment, such as addition of a solvent that can later be removed) to temporarily soften a polymer that has already been created. When softened in this manner, some polymers can be physically manipulated, in a manner that will allow reinforcing fibers to be subjected to a biasing step, and then allowed to cool or otherwise set in a manner that causes them to solidify into a modified configuration.

Any other currently-known or hereafter-discovered technique or device that provides additional options for use during a molding procedure can also be evaluated for use as described herein. For example, some types of molding operations utilize a specialized "releasing film", which is placed between a molding surface and a moldable material, to ensure that the moldable material does not adhere to the molding surface. Alternately or additionally, one or more types of post-setting procedures (often referred to as finishing or polishing steps, or similar terms) can also be evaluated for use herein. As one example, application of infrared radiation or other sources of heat can cause the surface of a gelatinous material to soften somewhat, in a manner that may help ensure a completely smooth and flat surface without disturbing or altering a tufting bias that has been imparted to tufting strands that are positioned below the surface of the gel material.

EXAMPLES

Example 1

Circular Stitched Prototypes

A number of test runs were carried out, using an AMAYA computer-controlled stitching machine under the control of a person who had not previously worked with such a machine, but who was familiar with home-type sewing, and who had attended the basic introductory training program on how to work the machine. Roughly two dozen trials were run, each one taking only a few minutes for the machine to complete, once the instructions had been programmed into the machine. These trial runs were for general evaluation purposes only, and the resulting stitched arrays were not intended to be actually embedded in hydrogels that would be tested in vitro or in animals; therefore, these trial runs used conventional and inexpensive thread from a fabric store, which was stitched onto a conventional inexpensive woven cotton fabric as the backing layer.

Typically, the results of a small batch of trial runs (typically involving about 5 to 10 samples, made with various different input parameters that had been controlled by the operator, all of which were recorded in a table or spreadsheet format for comparison and evaluation purposes) were shown to the surgeon during each session when the surgeon and the machine operator met to discuss the progress of the project. Typically, each batch of samples would vary two or three parameters in particular, which had been chosen for evaluation by the surgeon and operator. Based on the apparent results for each batch of samples, the surgeon and operator would agree on which samples appeared to have the best traits, and the next set of samples would be made with those varied parameters being held constant, while other parameters were varied.

By the time roughly thirty circular or ring-shaped samples had been made and evaluated, the settings that were regarded as being suitable for testing and evaluation in subsequent work generally fell within the ranges listed below. All of these settings used interlocked stitching, created with the aid of a "floating bobbin" system beneath the fabric. Although some specific parameters use different systems, the numbers used for most parameters refer to "points", in which 10 points equals one millimeter of linear distance.

Fill density: 10 to 25
Fill stitch length: 5 to 15 provided samples that were fairly tightly packed; 20 to 40 provided samples that covered larger areas
Speed: 550 to 900 stitches/minute
Material thickness: 9 to 20
Run fill/feed: 100 to 130

In addition, various presser foot settings were tested, ranging from 0 to 10. As mentioned above, this parameter is not controlled by software or a computer; instead, it is adjusted by turning a mechanical wheel that is mounted on the stitching machine. Higher numbers, in presser foot settings, will lead to greater stitch lengths and heights, and settings of 5 and 10 generally provided good results, in the materials created in the initial testing stage.

The samples that were regarded as most promising usually had both a primary layer of stitching (which was stitched onto the backing layer in a first stitching operation), and a secondary layer of stitching (which was stitched onto the combined backing layer and primary stitching, after the primary stitching operation had been completed). This approach will create stitched fiber arrays that have greater height and thickness than single-layer stitching. To create stronger, more consistent, and more uniform products, it usually is preferred to have the secondary stitching layer oriented at an angle to the primary stitching layer (this is analogous to how plywood is created, with the wood fibers oriented in different directions in the layers of a sheet, for maximum overall strength). The angles that are most commonly used, to give a secondary stitching layer a different orientation compared to a primary stitching layer, are 45, 90, or 135 degrees. Several relatively long stitch lengths were tested for secondary stitching layers, in several of the samples (ranging up to 100 units, compared to 20 or 25 units for the primary stitching layer). Multi-layer stitching (i.e., using more than two layers) was not evaluated in the initial round of tests, using cotton threads and fabrics; however, multilayer stitching can be evaluated for use as described herein, if desired, and anyone testing that approach should evaluate both monofilaments and yarns to form the various layers, since they are likely to perform differently in such uses.

Example 2

Arc-Shaped Prototypes

Hydrogel implants to replace the arc-shaped meniscal cartilage segments in knees are not covered or claimed by this particular application; however, they are of active interest to the inventors herein, and are covered by other patents and patent applications that remain active. Accordingly, a number of arc-shaped prototypes were created and evaluated, using inexpensive cotton thread and fabric as described in Example 1, to narrow down the range of parameters that would need to be tested after trials began with more expensive medical-grade fibers and fabrics.

The samples that were regarded as most promising, and worth subsequent evaluation, generally used lower fill densities (in a range of about 13 to 16), while run fill/feed settings of 110 were used in the most promising samples. Fill stitch lengths ranging from 20 to 85 were tested; although they give very different appearances, none were clearly and obviously unsuitable, and the midpoint of that range is regarded as a suitable range for testing, using medical-grade fibers and backing layers to create reinforced hydrogels that will be tested for strength and durability.

Bilayer and multilayer stitching were not tested in this initial round of arc-shaped segment tests; however, that approach is believed to be promising, for creating 3D fiber arrays having the thicknesses that will be required to adequately reinforce meniscal wedges, which generally are thicker (at their thickest points) than the relatively thin layers of hyaline cartilage that coat the bone surfaces in mammalian joints.

Thus, there has been shown and described a new and useful type of 3D fiber array, to reinforce hydrogel layers in surgical implants designed to replace hyaline cartilage, which can be created by specialized machines at low cost. Although this invention has been exemplified for purposes of illustration and description by reference to certain specific embodiments, it will be apparent to those skilled in the art that various modifications, alterations, and equivalents of the illustrated embodiments are possible. Any such changes which derive from the teachings herein, and which do not depart from the spirit and scope of the invention, are deemed to be covered by this invention.

REFERENCES

Clark, J. M., et al, "The organisation of collagen fibrils in the superficial zones of articular cartilage," *J. Anatomy* 171: 117-130 (1990)

Clark, J. M., et al, "Variation of collagen fiber alignment in a joint surface: A scanning electron microscope study of the tibial plateau in dog, rabbit, and man," *J. Orthopaedic Research* 9: 246-257 (1991)

Karamuk, E., et al, "Embroidery technology for medical textiles and tissue engineering," *Technical Textiles International, July/August* 2000: 9-12

Lange, J., et al, "Results of SaluCartilage implantation for stage IV chondral defects in the knee joint area," *Unfallchirurg.* 108(11): (e-published Nov. 23, 2005)

McQuaid, M., "Stronger," pp. 50-55 in *Extreme Textiles* (Princeton Architectural Press, New York City, 2004)

Meyer, C., et al, "Dislocation of artificial cartilage (SaluCartilage)," *Unfallchirurg.* 108(2): 163-6 (2005)

The invention claimed is:

1. An article of manufacture for surgical implantation into a mammalian joint to replace hyaline cartilage, comprising:
    a hydrogel material reinforced by a three-dimensional fiber array embedded within at least a portion of said hydrogel material;
    wherein the three-dimensional fiber array comprises a backing layer and a plurality of stitches that pass through said backing layer and are affixed to said backing layer.

2. The article of claim 1, wherein at least a portion of said three-dimensional fiber array comprises tufted loops.

3. The article of claim 1, wherein at least a portion of said three-dimensional fiber array comprises sewn stitches.

4. The article of claim 1, wherein said three-dimensional fiber array is affixed to an anchoring device that is designed, sized, and suited for surgical anchoring to a bone surface.

5. The article of claim 1, wherein said three-dimensional fiber array is affixed to an anchoring device that is designed, sized, and suited for surgical anchoring to a bone surface.

6. The article of claim 1, wherein said three-dimensional fiber array comprises a margin of unstitched backing material around at least a portion of its periphery.

7. The article of claim 5, wherein said three-dimensional fiber array is affixed to said anchoring device by means of an ultrasonically-welded attachment between a portion of said backing layer, and a polymeric component of said anchoring device.

8. The article of claim 1, wherein at least a portion of said plurality of stitches have been created by a computer-controlled stitching machine.

9. The article of claim 1, wherein said hydrogel material is a hydrophilic formulation of a polymer selected from the group consisting of polyacrylonitrile polymers and polyurethane polymers.

10. The article of claim 1, wherein the hydrogel material comprises at least one smooth surface that has no fibers exposed on said smooth surface.

11. An article of manufacture for surgical implantation into a mammalian joint to replace hyaline cartilage, comprising:
    a hydrogel material reinforced by a three-dimensional fiber array;
    wherein the three-dimensional fiber array includes a fiber height that extends into the hydrogel material and is embedded in the hydrogel material, a layer adjacent to a bottom of the three-dimensional fiber array, facing the hydrogel material, that is nonporous to intrusion of the hydrogel material, and an exposed bottom surface, opposite from the layer facing the hydrogel material, that is porous for encouraging tissue ingrowth; and,
wherein at least a portion of the three-dimensional fiber array comprises one of tufted loop and sewn stitches.

12. The article of claim 11, wherein said hydrogel material is a hydrophilic formulation of a polymer selected from the group consisting of polyacrylonitrile polymers and polyurethane polymers.

13. The article of claim 11, wherein the hydrogel material forms a smooth surface on a side opposite from the bottom surface, an upper extent of the fiber height being below said smooth surface.

14. The article of claim 11, wherein a plurality of stitches pass through and are affixed to said layer adjacent to the bottom of the three-dimensional fiber array.

* * * * *